US010172793B2

(12) United States Patent
Henriksen et al.

(10) Patent No.: US 10,172,793 B2
(45) Date of Patent: Jan. 8, 2019

(54) PROBIOTIC TABLET FORMULATIONS

(75) Inventors: Kristian Lund Henriksen, Søborg (DK); Helene Mathilda Mortensen, Vanløse (DK); Marianne Winning, Kokkedal (DK)

(73) Assignee: Ferrosan A.S. (DK)

( * ) Notice: Subject to any disclaimer, the term of this patent is extended or adjusted under 35 U.S.C. 154(b) by 2303 days.

(21) Appl. No.: 10/584,113

(22) PCT Filed: Dec. 21, 2004

(86) PCT No.: PCT/EP2004/014545
§ 371 (c)(1),
(2), (4) Date: Apr. 4, 2007

(87) PCT Pub. No.: WO2005/063200
PCT Pub. Date: Jul. 14, 2005

(65) Prior Publication Data
US 2007/0269515 A1 Nov. 22, 2007

(30) Foreign Application Priority Data
Dec. 24, 2003 (GB) .................................. 0330009.2

(51) Int. Cl.
A61K 9/28 (2006.01)
A61K 33/04 (2006.01)
A61K 9/00 (2006.01)
A61K 9/24 (2006.01)

(52) U.S. Cl.
CPC ............ A61K 9/0056 (2013.01); A61K 9/209 (2013.01)

(58) Field of Classification Search
None
See application file for complete search history.

(56) References Cited

U.S. PATENT DOCUMENTS

| | | | | |
|---|---|---|---|---|
| 4,314,995 A | * | 2/1982 | Hata et al. | 424/93.45 |
| 5,525,634 A | * | 6/1996 | Sintov et al. | 514/777 |
| 5,774,056 A | | 6/1998 | Berry | 340/607 |
| 5,885,481 A | | 3/1999 | Venkateshwaran | 252/188.28 |
| 6,068,855 A | | 5/2000 | Leslie | 424/468 |
| 6,083,585 A | | 7/2000 | Cahill | 428/35.7 |
| 6,228,397 B1 | | 5/2001 | Shen | 424/474 |
| 6,254,886 B1 | | 7/2001 | Fusca et al. | 424/464 |
| 6,399,114 B2 | | 6/2002 | Foreman | 424/93.3 |
| 7,037,708 B1 | * | 5/2006 | Runge et al. | 435/243 |
| 2003/0147857 A1 | * | 8/2003 | Monte | 424/93.4 |

FOREIGN PATENT DOCUMENTS

| | | | | |
|---|---|---|---|---|
| DE | 10206995 A1 | | 2/2002 | ............ A23L 1/30 |
| DE | 20202562 U1 | | 2/2002 | ............ A23L 1/30 |
| EP | 0255725 | * | 2/1988 | ............ A61K 9/22 |
| EP | 1072285 A1 | | 7/1999 | ............ A61K 9/48 |
| EP | 0956858 A | | 11/1999 | ............ A61K 35/74 |
| EP | 1449525 | * | 8/2004 | ............ A61K 9/24 |
| GB | 2323532 A | | 9/1998 | ............ A61K 35/74 |
| WO | WO 97/07822 | | 6/1997 | ............ A61K 47/26 |
| WO | WO 99/57242 | * | 11/1999 | ............ C12N 1/20 |
| WO | WO 00/07606 | | 2/2000 | ............ A61K 35/74 |
| WO | WO 01/15714 A1 | | 3/2001 | ............ A61K 35/74 |
| WO | WO 01/37880 A1 | | 5/2001 | ............ A61K 47/36 |
| WO | WO 02/39834 A1 | | 5/2002 | ............ A23L 1/29 |
| WO | WO 03/026687 A1 | | 4/2003 | ............ A61K 38/44 |
| WO | WO 03/080813 A2 | | 10/2003 | ............ C12N 1/20 |

OTHER PUBLICATIONS

Giagau et al., machine translation of DE 10206995-from IDS, description pp. 1-9, claims pp. 1-5.*
Belicova et al., "Synergic Activity of Selenium and Probiotic Bacterium Enterococcus faecium M-74 against Selected Mutagens in *Salmonella* Assay", Folia Microbiol., 2004, vol. 49, No. 3, pp. 301-305.*
Calomme et al., "*Selenium* and *Lactobacillus* species", Journal of Applied Bacteriology, 1995, vol. 79, pp. 331-340.*
Yang et al., "Antibacterial Action of Selenium-Enriched Probiotics Against pathogenic *Escherichia coli*", Digestive Diseases and Sciences, 2009, vol. 54, Issue 2, pp. 246-254.*
Belicova et al., "Synergic Activity of Selenium and Probiotic Bacterium Enterococcus faecium M-74 against Selected Mutagens in *Salmonella* Assay", Folia Microbiologica, 2004, vol. 49, No. 3, pp. 301-305.*
Published PCT International Search Report; WO 2005/063200 A3, dated Jul. 14, 2005.
Google.com translation, Giagau et al., DE 10206995 pp. 1-6, 2003.

* cited by examiner

*Primary Examiner* — Laura Schuberg
(74) *Attorney, Agent, or Firm* — Maureen P. O'Brien; Jeffrey M. Gold

(57) ABSTRACT

A probiotic tablet comprising a probiotic micro-organism and other nutritionally active ingredients in two zones, a first zone comprising said probiotic micro-organism and preicrably selenium, and a second zone comprising at least one said other active ingredient such as iron, other minerals and vitamin B6 kept separated from the probiotic micro-organism of said first zone, the water activity in said probiotic micro-organism containing first zone being no greater than 0.2 and the water content of said tablet being as much as 3% by weight. Good viability of the micro-organisms is obtained despite the relatively high overall moisture content.

50 Claims, No Drawings

PROBIOTIC TABLET FORMULATIONS

The present invention relates to the formulation of probiotic micro-organisms in tablet form. Probiotic micro-organisms are conventionally formulated with other nutritionally active materials such as vitamins, minerals, carbohydrates, proteins, co-enzymes, enzymes, plant extracts, trace elements, and/or fats. Whilst many probiotic micro-organisms are quite stable when kept by themselves in a dried form, tablet formulations in which the probiotic micro-organisms are mixed with active ingredients of the above kinds are highly unstable. After even brief storage, the recovery of viable micro-organisms upon rehydration of such mixed formulations will be extremely poor.

U.S. Pat. No. 6,254,886 attempts to address this problem by proposing that the tablet should be in a multilayer form with the probiotic micro-organism being contained in a layer which is free from other nutritionally active materials and which is dry to the extent that its water content is less than 0.1%. Since water is in fact free to move between the different layers of the tablet, this in practice means that the carrier material for all the tablet layers has to be dry to this same extent. Moreover, where large amounts of other active ingredients are present, they too will have to be aggressively dried if the total water content of the probiotic layer is not to rise significantly above the limits set in U.S. Pat. No. 6,254,886.

We have now found that the water content in a storage stable probiotic tablet formulation can be very much higher than is taught in U.S. Pat. No. 6,254,886 provided that care is taken that the water activity is maintained below 0.2 (equivalent to 20% relative humidity) and that the mixing with the probiotic micro-organisms of certain active materials taught to be kept separate from the probiotic micro-organisms in U.S. Pat. No. 6,254,886, is not deleterious and may actually improve the viability of the micro-organisms.

The present invention now provides a probiotic tablet comprising a probiotic micro-organism and other nutritionally active ingredients, the tablet comprising at least two zones, a first of said zones comprising said probiotic micro-organism, and a second of said zones comprising at least one said other active ingredient kept separated from the probiotic micro-organism of said first zone, the water activity in said probiotic micro-organism containing first zone being no greater than 0.2 and the water content of said tablet being no less than 0.2% by weight.

Tablets according to the invention, particularly as exemplified below may be storage stable at a cool temperature (up to 15° C.) or more preferably at room temperature (up to 20° C. or more preferably up to 25° C.) for several months, e.g. for up to one year or more preferably up to 18 months or more preferably two years or more. By 'storage stable' is meant that after a storage period, the number of viable probiotic micro-organisms should not have declined by more than a factor of one thousand, preferably not more than one hundred, more preferably not by a factor of more than 10 e.g. from $5*10^9$ to $5*10^8$, or less preferably to $5*10^7$ or still less preferably to $5*10^6$.

According to U.S. Pat. No. 6,254,886, the presence together with the probiotic micro-organism of other substances valuable in nutritional physiology is deleterious. It is suggested that at best there may be some unidentified active materials that are not deleterious. However, we have found that certain active materials actually improve the stability of the product when they are present in the first zone. In accordance with this, it is preferred that said first zone contains also selenium as a said at least one other active ingredient. Preferably, said first zone contains from 1 to 100 µg, e.g. 5 to 75 µg, more preferably 7.5 to 60 µg, of selenium, per $10^9$ micro-organisms.

The presence of selenium together with the micro-organisms is particularly preferred as we have demonstrated that selenium increases the storage stability of the tabletted micro-organisms. The mechanism responsible for this is at present uncertain. It may be that the selenium exerts a beneficial influence in one or more of several ways including as a growth medium, as a compression distributor, as a stabiliser, as a desiccant or as an antioxidant.

The presence in said first zone of antioxidants generally is also preferred. These include ascorbyl palmitate or other ascorbates, propyl gallates or other—gallates, alpha-tocopherol, magnesium or sodium sulfite, butylated hydroxyanisole or butylated hydroxytoluene.

Certain active ingredients are however deleterious and should preferably be excluded from the first zone. These include iron, vitamin B6, vitamin C, zinc, copper, manganese, chromium, pantothenic acid or its salts, and to a lesser extent vitamin B1, so the first zone is preferably free from amounts of some or all of each of these that are sufficient materially to exert an adverse effect on the stability of the product. Several of these materials are available in a micro-encapsulated form. One way in which such materials may be present in a tablet according to the invention without their being present in the first zone is for them to be encapsulated, but to be present as micro-particles mixed in to the probiotic micro-organism containing material. If the level of separation imposed by the micro-encapsulation of these materials is not adequate, they may still exert an adverse effect, so we prefer that they should not be mixed into the first zone in micro-encapsulated form, but should be relegated to a more physically distinct and separate macro-region of the tablet, such as a distinct layer. This applies especially to iron and copper.

Encapsulated zinc is better tolerated and can be admixed into the first zone materials.

Vitamin B1 can be present in the first zone in non-encapsulated form without much deleterious effect.

Some benefit may come from having certain encapsulated materials mixed into the first zone. These include micro-encapsulated vitamin B1, micro-encapsulated vitamin B6, micro-encapsulated zinc, micro-encapsulated manganese, micro-encapsulated vitamins A, D, E, B12 and B2.

Said second zone preferably contains as at least one said other active ingredient any one of iron, vitamin B6, vitamin C, zinc, copper, manganese, chromium, and pantothenic acid or a salt thereof. Preferably at least two, more preferably at least four, more preferably at least six and preferably all of these are present.

It is preferred that the tablets of the invention have a multi-layer form comprising two or more layers, one of said layers constituting said first zone and another of said layers constituting said second zone. Additional layers may be present. The layers may be formed one over the other or such that a body of material constituting one of the first and second zones is enrobed by a layer of material constituting the other of said zones.

Where such a two layer structure is used, it is still possible for the layer constituting said first zone to contain in encapsulated form some materials which are required to be kept out of the first zone, but for better separation of the probiotic micro-organisms from these materials it is preferred that they are not present mixed within the first zone layer but are present only in the second zone. This reduces the interface area between zones containing the probiotic micro-organism and these potentially destabilising ingredients. These include particularly iron, encapsulated iron, vitamin B6, vitamin C, zinc, copper, manganese, chromium, pantothenic acid and its salts, and encapsulated copper and to a lesser degree encapsulated zinc, especially if not strongly encapsulated, and vitamin B1.

On the other hand, it may be acceptable or even beneficial if mixed within the layer constituting the first zone are one, two or any combination of micro-encapsulated vitamin B1, micro-encapsulated vitamin B6, selenium, micro-encapsulated zinc, iodine, micro-encapsulated vitamins A, D, E, B12 or B2, nicotinamide, folic acid, or any of the anti-oxidants mentioned herein.

Summing this up, if one were to categorise other active ingredients likely to be present into three lists: A(aggressive ingredients to be kept well away from the probiotic material, e.g. in a separate layer), B (somewhat aggressive ingredients which are preferably excluded from the first zone, but which may well be tolerated either in the first zone or in micro-encapsulated form surrounded by the first zone) and C (non-aggressive or beneficial ingredients that can be present in the first zone or if encapsulated can be surrounded by the first zone) these lists would be as follows:

List A
iron
Encapsulated Fe
Vitamin B6
Vitamin C
Zinc
Copper
Manganese
Chromium
Calcium pantothenate
Encapsulated copper
List B
Vitamin B1
Nicotinamide
List C
Encapsulated vitamin B1
Encapsulated vitamin B6
Selenium
Encapsulated zinc
Iodine
Magnesium
Encapsulated manganese
Encapsulated vitamin A, D, E, B12, B2
Folic acid
Whilst not as well tolerated as the above ingredients in List C, nicotinamide may be categorised either in List B or in List C as may encapsulated zinc.

Whilst layer structures are preferred, it is permissible for the tablet to have a multitude of granules constituting said first zone surrounded by a matrix, wherein said matrix constitutes said second zone or wherein said matrix also contains a multitude of granules constituting said second zone.

In order to obtain a low water activity in the first zone, the probiotic micro-organism is preferably mixed with a desiccant carrier material serving to reduce the water activity of the zone containing the probiotic micro-organism. Optionally however such a desiccant carrier material serving to reduce the water activity of the zone containing the probiotic micro-organism may be present instead in the second zone. Preferably, such a material is present in both the first and second zones. The effect of such a desiccant may be to sequester part of the water content of the zone so that it is no longer in the form of free water that can migrate into the probiotic micro-organisms and is therefore prevented from carrying active substances through the cell walls of such organisms. Such desiccants bind water to specific sites so that it is no longer able to act as a solvent. These sites include the hydroxyl groups of polysaccharides, the carbonyl and amino groups of proteins, and others on which water can be held by hydrogen bonding, by ion-dipole bonds, or by other strong interactions. Thus, preferred desiccants include at least one of carboxymethylcellulose, colloidal silica, polyvinylpyrrolidone, starch, gelatine, hydroxypropylcellulose, microcrystalline cellulose, fumed silicon dioxide, sodium croscarmellose, crospovidone, povidone, magnesium aluminium silicate, methylcellulose, sodium alginate, sodium starch glyconate, sodium starch glycolate, gelatine, pregelatinized starch, or sorbitol. The desiccant may be in particular, a starch selected from corn, rice, or potato starch, a hydrophilic gum, polysaccharide or galactomannan such as pectin, agar, dextran, maltodextrin, carageenan, tragacanth gum, locust bean gum, acacia gum, guar gum, xanthan gum, ghatti gum, alginic acid or sodium alginate, a cellulose derivative such as methyl cellulose, carboxymethylcellulose, sodium starch glycollate, sodium or calcium carboxymethylcellulose, hydroxyethyl methylcellulose, hydroxypropylmethylcellulose, ethylhydroxyethylcellulose, ethylmethylcellulose, hydroxyethylcellulose, cellulose acetate phthalate, or microcrystalline cellulose, silica, aluminium silicate, magnesium silicate, aluminium magnesium silicate, sodium silicate or feldspar, aluminium hydroxide, a protein such as gelatin or casein or a polymer such as acrylate, carboxypolymethylene, a polyalkylene glycol or polyvinylpyrrolidone. Other steps to reduce the amount of oxygen present may be beneficial, including packing under an inert atmosphere such as nitrogen and the use of oxygen barrier packaging materials such as aluminium tubes or high barrier polymers.

The water content of the tablet is at least 0.2% by weight and may be considerably higher. Higher water contents remove the need for aggressive drying of materials which may be sensitive to such a process. It is undesirable that the water content in the tablet is too high as it increases the risk of unforeseen re-crystallisation. Also, it is expensive to remove water. Thus, the water content can be above 0.5% or above 1%, but below 6% more preferably below 5%, or 4%, 3% ,or even 2%. Alternatively, the water content can be above 0.5% or above 1% or 2% , but below 6% more preferably below 5%, or 4%, or 3%. Alternatively, the water content can be above 0.5% or above 1% or 2% or 3%, but below 6% more preferably below 5%, or 4%. The water content can go up to 7% by weight.

At the same time, the water activity is preferably below 0.18, more preferably below 0.15, still more preferably below 0.13, e.g. 0.10, or even 0.08. The water activity may be still lower, e.g. 0.05 or even 0.02. The water activity may lie between 0.2 and any of the foregoing figures or between any two of them.

Each of the foregoing figures for water activity relate to the first zone of the tablet. Normally, following internal equilibration, this will also be the water activity of the tablet as a whole. Unless an internal water excluding barrier layer is present separating off the first zone, the water activity will equilibrate throughout the tablet to reach the same value throughout.

To improve the separation of the probiotic micro-organisms from the ingredients that are hostile to their stability, said first zone may be separated from said second zone by a water excluding barrier material. Additionally or instead, the tablet as a whole may be surrounded by a water excluding material. Such materials may be cellulose acetate phthalate, methacrylic acid copolymers, alginic acid, zein, modified starch, polyvinylacetate phthallate, hydroxypropylmethylcellulose phthalate, cellulose acetate phtnaiate, or shellac.

The barrier materials may more preferably be or include a fat based material, which may be applied by a process of hot melt coating. These include but are not limited to fatty acid triglycerides, e.g. hydrogenated palm oil or beef tallow and mixtures of triglyceride esters of higher saturated fatty acids along with varying proportions of mono- and di-glycerides, e.g. hard fats.

Tablets according to the invention may be stored in a container containing a desiccant for absorbing water so as to reduce the water activity in the area surrounding said tablet. Thus, the tablets may be packaged in such a way as to preserve their initial state of dryness within acceptable limits. This may involve packaging the tablets in a moisture impermeable container such as a tube or a blister pack, which may contain a desiccant agent such as silica gel. For protection against oxygen such a pack may contain an oxygen scavenger material such as Amosorb™, ascorbyl palmitate or other ascorbates, propyl galates or other -gallates, alpha-tocopherol, magnesium or sodium sulfite, butylated hydroxyanisole or butylated hydroxytoluene. Oxygen absorbents as described in U.S. Pat. Nos. 5,885,481, 5,744,056, or 6,083,585 can be used.

The tablets may contain additional materials, especially in the second zone, such as plant materials, including herb materials, for example *Echinacea*, elderberry extract, blueberry extract, cranberry extract and rose hip.

The term 'probiotic micro-organism' is well understood by those skilled in the art to which this invention pertains. Probiotics are micro organisms, which in tablet formulations are normally freeze dried and are normally live, which have a beneficial effect on health when ingested. The probiotic micro-organisms may be lactic acid producing bacteria, e.g. *Lactobacilli* and *Bifidobacteria* bacteria. Probiotic micro-organisms that may be present include but are not limited to:

*Bibidobacterium*
   *bifidum*
   *longum*
   *adolescentis*
   *animalis*
   *infantis*
   *breve*
   *lactis*
*Lactobacillus*
   *casei*
   *acidophilus*
   *paracacei*
   *plantarum*
   *rhamnosus*
   *reuteri*
   *gasseri*
   *jensenii*
   *delbruekii* including subspecies *delbrueckii* and *bulgaricus*
   *helveticus*
   *salivarius*
   *brevis*
   *johnsonii*
   *crispatus*
*Bacillus*
   *coagulans*
*Saccharomyces*
   *boulaardii*
   *cerevisiae*
*Streptococcus*
   *thermnophilus*
*Enterococcus*
   *faecium*
   *faecalis*
*Propionebacterium*
   *freudenreichii*
Lactococcus
   *lactis*
*Propionebacterium*
   *fieudenreicii*

Each tablet suitably will contain from $10^6$, more preferably from $10^7$ to $10^{12}$, e.g. from $10^8$ to $10^{10}$, viable micro-organism cells.

Preferred methods for producing tablets from the tablet ingredients include standard tabletting methods, including those conventionally used for producing multi-layer tablets. As we have found that excessive tabletting pressure can decrease the viability of the micro-organisms, we prefer that the compression pressure for the probiotic layer should not exceed 50 kN/cm$^2$, corresponding to a tensile strength below 100N (Erweka equipment).

The tablets may be designed to be chewed or to be swallowed whole. When the tablets disintegrate on consumption, whether in the mouth or in the stomach, the micro-organisms are exposed to the materials from which they were held separate in the tablet structure. This may harm the micro-organisms if the local concentration of the damaging materials is too high. To guard against this, it is preferred that the disintegration of the two zones or layers be spaced in time to a degree to allow the contents of one zone to be diluted and dispersed before the other zone is released. This may be achieved by the inclusion in one zone or layer of disintegrant agents selected to provide faster disintegration of that zone. The effect may be quantitated by a dissolution test in which a tablet is allowed to disintegrate in unstirred water in a beaker at 25° C. and after one zone has disintegrated, the remainder of the tablet is removed, dried and weighed to establish the amount of that zone of the tablet remaining (as a proportion of the total amount of that zone initially). Preferably, in such a test, the remainder should amount to no less than 20%, more preferably no less than 50%, most preferably no less than 70% of the original amount of that zone or layer.

The test may alternatively be conducted on a time measurement basis in which the tablet is allowed to dissolve as before but the time when a first zone has disintegrated is noted and the time when the total tablet has disintegrated is noted. If both layers disintegrated at the same rate, the first time period would be the same as the total disintegration time. When one zone disintegrates faster, as preferred, the first time period as a percentage of the total disintegration time is preferably no more than 50%, more preferably no more than 20% and most preferably no more than 5% of the total.

Ingredients that promote rapid disintegration (super-disintegrants) that can be included in one of the zones for this purpose include sodium croscarmellose, cross linked sodium carboxymethylcellulose, crospovidone, sodium starch gycolate, sodium starch glycolate and pregelatinized starch.

The invention will be further described with reference to the following illustrative examples of multilayer tablets, containing freeze dried probiotic cultures and vitamins/minerals, herbals or drugs.

EXAMPLE 1

The following ingredients were formulated into a two layer tasty chewable tablet incorporating lactic acid bacteria, vitamins and minerals using Xylitol and Isomalt to provide bulk and sweetening:

Per Tablet:
Vitamin A mcg 700.00 Retinolacetate
Vitamin D mcg 5.00 Cholecalciferol
Vitamin E IU 10.43 D,L-alfa-tocopherolacetate
Vitamin B1 (salt) mg 1.00 Thiaminenitrate
Vitamin B2 mg 1.20 Riboflavin
Vitamin B6(salt) mg 1.10 Pyridoxine chloride
Vitamin B12 mcg 1.40 Cyanocobalamin
Nicotinamide mg 13.00 Nicotinamide
Pantothenic acid mg 5.00 D-Calcium pantothenate
Folic acid mcg 100.00 Folic acid
Vitamin C mg 60.00 Ascorbic acid
Calcium mg 200.00 Calcium carbonate
Magnesium mg 50.00 Magnesium oxide
Iron mg 10.00 Ferrous fumarate
Zinc mg 7.00 Zinc oxide
Copper mg 0.70 Cupric oxide
Manganese mg 2.00 Manganese sulfate
Chromium mcg 50.00 Chromium (III) chloride
Selenium mcg 30.00 Sodium selenate
Iodine mcg 90.00 Potassium iodide
Biotin mcg 30.00 d-Biotin
Vitamin K mcg 30.00 Phytomenadione
Lactobacillus GG cfa $1 \times 10^9$ The vitamins and minerals (except for selenium) are mixed with the following excipients:

| | |
|---|---|
| Xylitol | 320 mg |
| Microcrystalline cellulose | 64 mg |
| Flavour | 33 mg |
| Stearic acid | 22 mg |
| Silicon dioxide | 7 mg |
| Acesulfam potassium | 2 mg |
| (in total | 700 mg) |

The freeze dried probiotic culture (10 mg=$3 \times 10^9$) and the selenium is mixed with:

| | |
|---|---|
| Isomalt | 253 mg |
| Xylitol | 100 mg |
| Microcrystalline cellulose | 31 mg |
| Magnesium stearate | 4 mg |
| silicon dioxide | 2 mg |
| (in total | 400 mg) |

Tablets were produced having two superposed layers using a conventional tabletting machine, the ingredients of one layer being filled over the ingredients of the other.

| | |
|---|---|
| Tablet weight | 1100 mg |
| Tablet size | 11 by 16.5 mm oval |
| Water activity** in culture granulate | <0.1 |
| Water content* in culture granulate | 2% |
| Water activity** in tablet | 0.09 |
| Water content* in tablet | 2.7% |

**Nova Sina . . . ,
*Karl Fisher

For comparison, a single layer tablet was produced containing the same ingredients. The viability of the microorganisms was measured after storage of the tablets over nine months with the following results:

| Months | Single layer tablet | Dual layer tablet |
|---|---|---|
| 0 | $7.3 * 10^8$ | $1.5 * 10^9$ |
| 1.5 | $6.9 * 10^7$ | $1.1 * 10^9$ |
| 6 | $1.5 * 10^7$ | $3.4 * 10^7$ |
| 9 | $<2 * 10^3$ | $1.1 * 10^5$ |

It can be seen that the two layer tablet of the invention maintained the viability of the micro-organisms over the total storage period better by a factor of over 100.

EXAMPLE 2

The following ingredients were formulated as a two layer tablet to swallow with lactic acid bacteria, vitamins and minerals.

Per Tablet:
Vitamin D mcg 5.00 Cholecalciferol
Vitamin E IU 14.90 D,L-alfatocopherolacetate
Vitamin B1 (salt) mg 5.00 Thiaminenitrate
Vitamin B2 mg 5.00 Riboflavin
Vitamin B6(salt) mg 5.00 Pyridoxinchloride
Vitamin B12 mcg 3.00 Cyanocobalamin
Biotin mcg 30.00 d-Biotin
Nicotinamide mg 18.00 Nicotinamide
Pantothenic acid mg 5.00 D-Calciumpantothenate
Folic acid mcg 400.00 Folic acid
Vitamin C mg 90.00 Ascorbic acid
Magnesium mg 90.00 Magnesium oxide
Zinc mg 15.00 Zinc oxide
Manganese mg 2.50 Manganese sulfate
Chromium mcg 30.00 Chromium (III) chloride
Selenium mcg 50.00 Sodium selenate
Iodine mcg 100.00 Calcium iodide
*Lactobacillus* GG cfu $1 \times 10^9$ The vitamins and minerals (except for selenium) are mixed with the following excipients:

| | |
|---|---|
| Microcrystalline cellulose | 58 mg |
| Magnesium stearate | 4 mg |
| Stearic acid | 3 mg |
| Silicon dioxide | 1 mg |
| (in total | 555 mg) |

The freeze dried probiotic culture (10 mg=$3 \times 10^9$) and the selenium are mixed with:

| | |
|---|---|
| Microcrystalline cellulose | 183 mg |
| Magnesium stearate | 2 mg |
| Silicon dioxide | 0.4 mg |
| (in total | 195 mg) |

Tabletting was conducted as in Example 1 and the 2-layer tablets were filled into aluminium tubes with desiccant in the lid.

| | |
|---|---|
| Tablet weight | 750 mg |
| Tablet size | 12 by 4 mm circular |
| Water activity** in culture granulate | 0.07 |
| Water content* in culture granulate | 2% |
| Water activity** in tablet | 0.07 |
| Water content* in tablet | 3.2% |

**Nova Sina . . . ,
*Karl Fisher

EXAMPLE 3

The following ingredients were formulated into a two layer tasty chewable tablet incorporating lactic acid bacteria, vitamins and minerals using Xylitol and Lactitol to provide bulk and sweetening:

Per Tablet:
Vitamin A mcg 700.00 Retinolacetate
Vitamin D mcg 5.00 Cholecalciferol
Vitamin E IU 10.43 D,L-alfa-tocopherol acetate
Vitamin B1 (salt) mg 1.00 Thiaminenitrate
Vitamin B2 mg 1.20 Riboflavin
Vitamin B6(salt) mg 1.10 Pyridoxine chloride
Vitamin B12 mcg 1.40 Cyanocobalamin
Nicotinamide mg 13.00 Nicotinamide
Pantothenic acid mg 5.00 D-Calcium pantothenate
Folic acid mcg 100.00 Folic acid
Vitamin C mg 60.00 Ascorbic acid
Calcium mg 200.00 Calcium carbonate
Magnesium mg 50.00 Magnesium oxide
Iron mg 10.00 Ferrous fumarate
Zinc mg 7.00 Zinc oxide
Copper mg 0.70 Cupric oxide
Manganese mg 2.00 Manganese sulfate
Chromium mcg 50.00 Chromium (III) chloride
Selenium mcg 30.00 Sodium selenate
Iodine mcg 90.00 Potassium iodide
Biotin mcg 30.00 d-Biotin
Vitamin K mcg 30.00 Phytomenadione
*Lactobacillus* GG cfu $1 \times 1^9$ The vitamins and minerals (except for selenium) are mixed with the following excipients:

| | |
|---|---|
| Lactitol | 209 mg |
| Microcrystalline cellulose | 39 mg |
| Flavour | 2.5 mg |
| Stearic acid | 44 mg |
| Silicon dioxide | 14 mg |
| Neohesperidin 10% | 0.2 mg |
| Citric acid monohydrate | 2 mg |
| (in total | 1160 mg) |

The freeze dried probiotic culture (10 mg=$3 \times 10^9$) and the selenium is mixed with:

| | |
|---|---|
| Lactitol | 394 mg |
| Microcrystalline cellulose | 21 mg |
| Stearic acid | 14 mg |
| (in total | 440 mg) |

Tabletting was conducted as in Example 1 and the 2-layer tablets were filled into aluminium tubes with desiccant in the lid.

| | |
|---|---|
| Tablet weight | 1600 mg |
| Tablet size | 16 mm circular |
| Water activity** in culture granulate | <0.1 |
| Water content* in culture granulate | 3.1% |
| Water activity** in tablet | 0.09 |
| Water content* in tablet | 3.7% |

**Nova Sina . . . ,
*Karl Fisher

The tablets were tested for stability by storage for 18 months in higher (24%), middle (20%) and lower (7%) relative humidity conditions and viability of the microorganisms was monitored, with the following results:

| Months | 24% humidity | 20% humidity | 7% humidity |
|---|---|---|---|
| 0 | $1.7 * 10^9$ | $1.7 * 10^9$ | $1.7 * 10^9$ |
| 6 | $8.7 * 10^6$ | $1.3 * 10^8$ | $0.9 * 10^9$ |
| 9 | $8.5 * 10^5$ | $8.0 * 10^8$ | $0.6 * 10^9$ |
| 12 | $1.4 * 10^4$ | $3 * 10^6$ | $0.6 * 10^9$ |
| 18 | $<2 * 10^3$ | $5.7 * 10^5$ | ND |

Thus, it can be seen that the tablets of the invention provided excellent long term stability.

In the above Examples, the vitamins used were in some cases supplied in an encapsulated form, others were used in non-encapsulated form. The table below indicates the ingredients present in the vitamin formulations used

| Active ingredients | Amount |
|---|---|
| Vitamin D (Cholecalciferol) | 5 mcg = 200 IU |
| As Cholecalciferol Concentrate Powder (analysed to 110 IU/mg) | 2.00 mg |
| Cholecalciferol | 6 mcg |
| Sucrose | 0.68 mg |
| Gelatin | 0.42 mg |
| Modified Starch | 0.42 mg |
| Triglycerides, medium-chain | 0.38 mg |
| Butyl Hydroxytoluene | 19 mcg |
| Sodium Aluminosilicate | 3 mcg |
| Water | 72 mcg |
| Vitamin E (D-α-tocopherol) | 14.90 IU |
| As α-Tocopherol Acetate Concentrate (Powder form)(analysed to 52.5 w/w %) | 30.08 mg |
| DL-α-Tocopherol Acetate | 15.79 mg |
| Maize Starch | 6.02 mg |
| Gelatin | 5.11 mg |
| Sucrose | 1.41 mg |
| Sodium Aluminosilicate | 0.39 mg |
| Water | 1.35 mg |
| Vitamin B1 (Thiamin) | 5 mg |
| As Thiamin Nitrate 33% | 14.85 mg |
| Thiamin nitrate | 4.95 mg |
| Mixture of mono-, di and triglycerides | 9.90 mg |
| Vitamin B2 (Riboflavin) | 5 mg |
| As Riboflavine 33% | 15.60 mg |
| Riboflavine | 5.20 mg |
| Mixture of mono-, di and triglycerides | 8.84 mg |
| Maize Starch | 1.56 mg |
| Vitamin B6 (Pyridoxine) | 5 mg |
| As Pyridoxine Hydrochloride 33% | 15.45 mg |
| Pyridoxine Hydrochloride | 5.15 mg |
| Mixture of mono-, di and triglycerides | 10.30 mg |
| Vitamin B12 | 3 mcg |
| As Cyanocobalamine 0.1% (analysed to 0.11%) | 1.87 mg |
| Cyanocobalamine | 3 mcg |
| Maltodextrin | 2.64 mg |
| Sodium citrate | 27 mcg |
| Citric acid | 20 mcg |
| Water | 120 mcg |
| Biotin | 30 mcg |
| As D-Biotin | 32 mcg |
| Nicotinamide | 18 mg |
| As Nicotinamide 33% | 56.16 mg |
| Nicotinamide | 18.72 mg |
| Mixture of mono-, di and triglycerides | 31.82 mg |
| Silicon dioxide | 5.62 mg |
| Pantothenic Acid | 5 mg |
| As Calcium Pantothenate | 5.56 mg |
| Folic Acid | 400 mcg |
| Folic Acid | 0.49 mg |

-continued

| Active ingredients | Amount |
|---|---|
| Folic Acid | 0.44 mg |
| Absorbed Water | 49 mcg |
| Vitamin C (Ascorbic Acid) | 90 mg |
| As Ascorbic Acid 97% | 100.21 mg |
| Ascorbic Acid | 97.20 mg |
| Maize Starch | 3.01 mg |
| Vitamin A (Retinol) | 700 mcg |
| Vitamin A Concentrate Synthetic (Powder form)(analysed to 565 IU/mg) | 5.21 mg |
| Retinol Acetate | 1.02 mg |
| Sucrose | 1.77 mg |
| Gelatin | 1.25 mg |
| Modified Starch | 0.83 mg |
| Butylated Hydroxytoluene | 0.07 mg |
| Sodium Aluminosilicate | 18 mcg |
| Water | 0.25 mg |

EXAMPLE 4

Effect of Selenium on Viability on Storage:

The following mixtures have been stored in a dehumidified room at a temperature of 25° C. Starting counts and counts of viable organisms after the indicated storage period were measured.

(a)
5 mg LGG+295 mg Microcrystalline cellulose:
Start week 0: count $3{,}5 \times 10^9$ Cfu/tablet
End week 8: count $2{,}9 \times 10^9$ Cfu/tablet (b)
5 mg LGG+0.05 mg Selenium+295 mg Microcrystalline cellulose:
Start week 0: count $4{,}0 \times 10^9$ Cfu/tablet
End week 8: $4{,}6 \times 10^9$ Cfu/tablet It can be seen that the presence of selenium was beneficial to the stability of the micro-organisms, and indeed that the numbers of recoverable micro-organisms even increased on storage in the presence of selenium.

In each case the probiotic bacteria were *Lactobacillus rhamnosus* GG "Grade P" (ATCC 53103) as a concentrated, freeze-dried bacterial powder.

EXAMPLE 5

Tablets with Differential Speed of Disintegration of Layers

The composition of the probiotic layer, but not of the vitamin/mineral layer, of the tablet of Example 2 was modified in three ways as follows:

Freeze dried probiotic culture and selenium—unchanged
Probiotic Layer Formulation (a)

| | |
|---|---|
| Selenium granulate 2% | 2.5 mg |
| Silicon dioxide | 0.4 mg |
| Lactose anhydrous | 181 mg |
| Magnesium stearate | 1.5 mg |

Probiotic Layer Formulation (b)

| | |
|---|---|
| Selenium granulate 2% | 2.5 mg |
| Silicon dioxide | 0.4 mg |
| Lactose anhydrous | 171.7 mg |
| Croscarmellose sodium | 1.5 mg |

Probiotic Layer Formulation (c)

| | |
|---|---|
| Selenium granulate 2% | 2.5 mg |
| Silicon dioxide | 0.4 mg |
| Lactose anhydrous | 171.7 mg |
| Magnesium stearate | 1.5 mg |
| Povidone | 9.3 mg |

The dissolution time of the two layers was measured in each case by observing disintegration of the tablet in a beaker of water with the following results:

| | |
|---|---|
| Vitamin/mineral layer: | 14 minutes |
| Probiotic layer: | |
| Formulation (a) | 6 minutes |
| Formulation (b) | 1 minute 45 sec |
| Formulation (c) | 15 sec |

EXAMPLE 6

Further Tablets with Differential Speed of Disintegration of Layers

A two layer tablet was produced in which a probiotic containing layer was formulated as follows:

| The freeze dried probiotic culture (10 mg = 3 × 109) is mixed with: | |
|---|---|
| Selenium Granulate 2% | 2.5 mg |
| Silicon Dioxide | 0.8 mg |
| Magnesium Stearate | 1.5 mg |
| Cellulose, Microcrystalline Cellulose | 152.4 mg |
| Hypromellose 15000 | 27.8 mg |

The vitamin/mineral layer was as from example 2 with either 0% Croscarmellose (Formulation 1) or 5% Croscarmellose Sodium (Formulation 2)

In a dissolution test conducted as above, the results were as follows:

| Disintegration time | |
|---|---|
| Probiotic layer | 10 minutes |
| Vitamin/mineral layer | |
| 1: | 37 minutes |
| 2: | 3 minutes |

The invention claimed is:

1. A probiotic tablet comprising a probiotic micro-organism, and other nutritionally active ingredients and excipients, the tablet comprising at least two zones, a first of said zones comprising said probiotic micro-organism in an amount of about $10^7$ to $10^{12}$ cells per tablet and selenium as a nutritionally active ingredient in an amount of about 30 to 60 micrograms per tablet, and a second of said zones comprising at least one said other active ingredient kept separated from the probiotic micro-organism of said first zone, the water activity in said probiotic micro-organism containing first zone being no greater than 0.2 and the water content of said tablet being no less than 0.2% by weight, and comprising in said second zone at least one material selected from the group consisting of iron, copper, chromium, zinc, vitamin B6, manganese, pantothenic acid and pantothenic acid salts as a said other active ingredient.

2. The tablet as claimed in claim 1, wherein said first zone is free from amounts deleterious to the viability of the probiotic micro-organisms of iron.

3. The tablet as claimed in claim 1, wherein said first zone is free from amounts deleterious to the viability of the probiotic micro-organisms of copper.

4. The tablet as claimed in claim 1, wherein said first zone is free from amounts deleterious to the viability of the probiotic micro-organisms of vitamin B6.

5. The tablet as claimed in claim 1, wherein said first zone is free from amounts deleterious to the viability of the probiotic micro-organisms of vitamin C.

6. The tablet as claimed in claim 1, wherein said first zone is free from amounts deleterious to the viability of the probiotic micro-organisms of zinc.

7. The tablet as claimed in claim 1, wherein said first zone is free from amounts deleterious to the viability of the probiotic micro-organisms of manganese.

8. The tablet as claimed in claim 1, wherein said first zone is free from amounts deleterious to the viability of the probiotic micro-organisms of chromium.

9. The tablet as claimed in claim 1, wherein said first zone is free from amounts deleterious to the viability of the probiotic micro-organisms of pantothoenic acid or its salts.

10. The tablet as claimed in claim 1, wherein said second zone contains iron as at least one said other active ingredient.

11. The tablet as claimed in claim 1, wherein said second zone contains vitamin B6 as at least one said other active ingredient.

12. The tablet as claimed in claim 1, wherein said second zone contains vitamin C as at least one said other active ingredient.

13. The tablet as claimed in claim 1, wherein said second zone contains copper as at least one said other active ingredient.

14. The tablet as claimed in claim 1, wherein said second zone contains manganese as at least one said other active ingredient.

15. The tablet as claimed in claim 1, wherein said second zone contains pantothenic acid or a salt thereof as at least one said other active ingredient.

16. The tablet as claimed in claim 1, wherein said second zone contains zinc as at least one said other active ingredient.

17. The tablet as claimed in claim 1, wherein said second zone contains chromium as at least one said other active ingredient.

18. The tablet as claimed in claim 1, wherein said second zone contains any two or more of iron, vitamin B6, vitamin C, pantothenic acid or a salt thereof, zinc, copper, chromium and manganese, each as at least one said other active ingredient.

19. The tablet as claimed in claim 1, wherein the probiotic microorganism is mixed with a desiccant carrier material serving to reduce the water activity of the zone containing the probiotic micro-organism.

20. The tablet as claimed in claim 1, wherein the second zone contains a desiccant carrier material serving to reduce the water activity of the zone containing the probiotic micro-organism.

21. The tablet as claimed in claim 1, wherein the probiotic microorganism is mixed with a desiccant carrier material serving to reduce the water activity of the zone containing the probiotic micro-organism or wherein the second zone contains a desiccant carrier material serving to reduce the water activity of the zone containing the probiotic microorganism, and wherein said desiccant material comprises at least one of carboxymethylcellulose, colloidal silica, polyvinylpyrrolidone, starch, gelatine, hydroxypropylcellulose-low-substituted, microcrystalline cellulose, fumed silicon dioxide, sodium croscarmellose, crospovidone, povidone, magnesium aluminum silicate, methylcellulose, sodium alginate, sodium starch glyconate, gelatin, pregelatinized starch, or sorbitol.

22. The tablet as claimed in claim 1, having a multilayer structure comprising at least two layers, one of said layers constituting said first zone and another of said layers constituting said second zone.

23. The tablet as claimed in claim 22, wherein said layer constituting said first zone is free of encapsulated iron.

24. The tablet as claimed in claim 22, wherein said layer constituting said first zone is free of encapsulated zinc.

25. The tablet as claimed in claim 22, wherein said layer constituting said first zone is free of encapsulated copper.

26. The tablet as claimed in claim 22, wherein said layer constituting said first zone contains encapsulated vitamin B1.

27. The tablet as claimed in claim 22, wherein said layer constituting said first zone contains encapsulated vitamin B6.

28. The tablet as claimed in claim 22, wherein said layer constituting said first zone contains encapsulated zinc.

29. The tablet as claimed in claim 22, wherein said layer constituting said first zone contains encapsulated manganese.

30. The tablet as claimed in claim 22, wherein said layer constituting said first zone contains encapsulated vitamin A, D, E, B12 or B2.

31. The tablet as claimed in claim 1, having a multitude of granules constituting said first zone surrounded by a matrix, and wherein said matrix constitutes said second zone or wherein said matrix also contains a multitude of granules constituting said second zone.

32. The tablet as claimed in claim 1, wherein the water content of the tablet is at least 1% by weight.

33. The tablet as claimed in claim 1, wherein the water content of the tablet is at least 2% by weight.

34. The tablet as claimed in claim 1, wherein the water content of the tablet is at least 3% by weight.

35. The tablet as claimed in claim 1, wherein the water content of the tablet is at least 4% by weight.

36. The tablet as claimed in claim 1, wherein the water content of the tablet is at least 5% by weight.

37. The tablet as claimed in claim 1, wherein the water content of the tablet is at least 6% by weight.

38. The tablet as claimed in claim 1, wherein the water content of the tablet is at least 7% by weight.

39. The tablet as claimed in claim 1, wherein the water activity of said first zone is no greater than 0.15.

40. The tablet as claimed in claim 1, wherein the water activity of said first zone is no greater than 0.1.

41. The A tablet as claimed in claim 1, wherein the water activity of said first zone is no greater than 0.05.

42. The tablet as claimed in claim 1, wherein the water activity of the tablet is below 0.15.

43. The tablet as claimed in claim 1, wherein said first zone is separated from said second zone by a water excluding barrier material.

44. The tablet as claimed in claim 43, wherein a said barrier material is a fat or wax based barrier material.

45. The tablet as claimed in claim 1, wherein the tablet is surrounded by a water excluding material.

46. The tablet as claimed in claim 1 stored in a container containing a desiccant for absorbing water so as to reduce the water activity in the area surrounding said tablet, and/or containing an oxygen scavenging agent and/or containing an inert gas atmosphere.

47. The tablet as claimed in claim 1, wherein said first zone contains also one or more of iodine, magnesium, nicotinamide and folic acid as a said at least one other active ingredient.

48. The tablet as claimed in claim 1, wherein upon immersion in water a first of said zones disintegrates at a faster rate than a second of said zones such that the time for disintegration of said faster disintegrating zone as a percentage of the total time for disintegration of the faster and the slower disintegrating zones is no more than 50%.

49. A probiotic tablet comprising a probiotic micro-organism, and other nutritionally active ingredients and excipients, the tablet comprising at least two zones, a first of said zones comprising said probiotic micro-organism in an amount of about $10^7$ to $10^{12}$ cells per tablet and selenium as a nutritionally active ingredient in an amount of about 30 to 60 micrograms per tablet, and a second of said zones comprising at least one said other active ingredient kept separated from the probiotic micro-organism of said first zone, the water activity in said probiotic micro-organism containing first zone being no greater than 0.02 and the water content of said tablet being no less than 0.2% by weight.

50. A probiotic tablet comprising a probiotic micro-organism, and other nutritionally active ingredients and excipients, the tablet comprising of at least two zones, a first of said zones comprising said probiotic micro-organism in an amount of about $10^7$ to $10^{12}$ cells per tablet and selenium as a nutritionally active ingredient in an amount of about 30 to 60 micrograms per tablet, and a second of said zones comprising at least one said other active ingredient kept separated from the probiotic micro-organism of said first zone, the water activity in said probiotic micro-organism containing first zone being no greater than 0.2 and the water content of said tablet being no less than 0.2% by weight.

* * * * *